United States Patent [19]
McMurry et al.

[11] Patent Number: 5,929,046
[45] Date of Patent: Jul. 27, 1999

[54] PYRIMIDINE AND PURINE DERIVATIVES AND THEIR USE IN TREATING TUMOUR CELLS

[75] Inventors: Thomas Brian Hamilton McMurry, Killiney; Robert Stanley McElhinney, Delgany; Dorothy Josephine Donnelly, Dublin; Paul Murray, Nurney, all of Ireland; Christophe Carola, St. Leu-la-Foret, France; Rhoderick Hugh Elder, Cheshire, United Kingdom; Jane Kelly, Manchester, United Kingdom; Geoffrey Paul Margison, Poynton, United Kingdom; Joseph Anthony Rafferty, Stockport, United Kingdom; Amanda Jean Watson, Cheshire, United Kingdom; Mark Andrew Willington, Cheshire, United Kingdom

[73] Assignee: Cancer Research Campaign Technology Limited, London, United Kingdom

[21] Appl. No.: 08/572,966

[22] Filed: Dec. 15, 1995

Related U.S. Application Data

[63] Continuation-in-part of application No. 08/568,576, Dec. 7, 1995, which is a continuation-in-part of application No. PCT/IE94/00031, Jun. 8, 1994.

[51] Int. Cl.$^6$ .......................... A61K 31/70; A61K 31/505; C07H 19/167; C07H 19/173; C07D 473/00
[52] U.S. Cl. .......................... 514/45; 514/274; 536/27.8; 536/27.81; 544/262; 544/309; 544/310; 544/313
[58] Field of Search .................. 514/45, 224; 536/27.8, 536/27.81; 544/262, 309, 310, 313

[56] References Cited

U.S. PATENT DOCUMENTS

| | | | |
|---|---|---|---|
| 4,772,606 | 9/1988 | Sircar et al. | 514/262 |
| 5,091,430 | 2/1992 | Moschel et al. | 514/262 |
| 5,260,291 | 11/1993 | Lunt et al. | 514/183 |
| 5,352,669 | 10/1994 | Moschel et al. | 514/45 |
| 5,358,952 | 10/1994 | Moschel et al. | 514/262 |
| 5,393,755 | 2/1995 | Neustadt et al. | 514/233.2 |
| 5,525,606 | 6/1996 | Moschel et al. | 514/262 |

FOREIGN PATENT DOCUMENTS

| | | |
|---|---|---|
| 184 473 A1 | 6/1986 | European Pat. Off. . |
| 2139107 | 2/1973 | Germany . |
| 91/13898 | 9/1991 | WIPO . |
| WO 91/13898 | 9/1991 | WIPO . |
| 94/29312 | 12/1994 | WIPO . |
| 9429312 | 12/1994 | WIPO . |
| WO 94/28312 | 12/1994 | WIPO . |
| WO 96/04281 | 2/1996 | WIPO . |

OTHER PUBLICATIONS

*Chemical Abstracts*, vol. 101, No. 25, Dec. 17, 1994, Abstract No. 230466q, p. 765, col. R. and *Heterocycles*, vol. 22, No. 8, 1984, pp. 1789–1790, Ram Siya et al.

J.F. Bunnett et al., "The Relative Reactivities of Methanol and Methoxide Ion in Addition to 4–Chlorobenzyne," *The Journal of Organic Chemical Chemistry*, vol. 34, No. 7, Jul. 1969, pp.2035–2163.

Chae et al. (I), "Substituted $O^6$—Benzyl Guanine Derivatives and Their Inactivation of Human $O^6$—Alkylguanine–DNA Alkyl Transferase," *J. Medicinal Chem.*, 37(3), 342–347 (1994).

Martinez et al., "Potential Antitumor Agents. Some Sulfur–Substituted Derivatives of α– and β–2'–Deoxythioguanosine," *J. Medicinal Chem.*, 20(3), 341–344 (1977).

Paul et al., "Inhibitors of Nucleoside Transport. A Structure–Activity Study Using Human Erythrocytes," *J. Medicinal Chem..*, 18(10), 968–973 (1975).

Moschel et al. (V), "Structural Features of Substituted Purine Derivatives Compatible with Depletion of Human $O^6$–Alkylguanine–DNA Alkyltransferase," *J. Medicinal Chem.*, 35(23), 4486–4491 (1992).

MacCoss et al., "Synthesis of the Chiral Acylonucleoside Antiherpetic Agent (S)–9–(2,3–Dihydroxy–1–Propoxymethyl)guanine," *Tetrahedron Letters*, 26(15), 1815–1818 (1985).

(List continued on next page.)

*Primary Examiner*—John Kight
*Assistant Examiner*—L. Eric Crane
*Attorney, Agent, or Firm*—Beveridge, DeGrandi, Weilacher & Young, LLP

[57] ABSTRACT

The present invention provides certain 6-hetarylalkyloxy pyrimidine derivatives of formula II

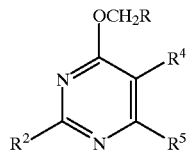

wherein R is (i) a cyclic group having at least one 5- or 6-membered heterocyclic ring, optionally with a carbocyclic or heterocyclic ring fused thereto, the or each heterocyclic ring having at least one hetero atom chosen from O, N, or S, or a substituted derivative thereof; or (ii) phenyl or a substituted derivative thereof, $R^2$ is selected from H, $C_1$–$C_5$ alkyl, halogen or $NH_2$, $R^4$ and $R^5$ which are the same or different are selected from H, $NH_2$ or $NO_n$ where n=1 or 2, or $R^4$ and $R^5$ together with the pyrimidine ring form a 5-or 6-membered ring structure containing one or more heterocyclic atoms, and pharmaceutically acceptable salts thereof, exhibit the ability to deplete $\underline{O}^6$-alkylguanine-DNA alkyltransferase (ATase) activity.

19 Claims, No Drawings

OTHER PUBLICATIONS

Dolan et al.(I), "Depletion of Mammalian $O^6$–Alklguanine–DNA Alkyltransferase Activity by $O^6$–Benzylguanine Provides a Means to Evaluate the Role of This Protein in Protection Against Carcinogenic and Therapeutic Alkylating Agents," *Proc. Nat. Acad. Sci. USA,* 87, 5368–5372 (Jul. 1990).

Dolan et al. (II), "Modulation of Mammalian $O^6$–Alkylguanine–DNA Alkyltransferase in vivo by $O^6$–Benzylguanine and its Effects on the Sensitivity of a Human Glimoa Tumor to 1–(2–chloroethyl)–3–(4–methylcyclohexyl)–1–nitrosourea," *Cancer Comm.,* 2(11), 371–377 (1990).

Dolan et al. (III), "Metabolism of $O^6$–Benzylguanine, an Inactivator of $O^6$–Alkylguanine–DNA Alkyltranferase," *Cancer Res.,* 54(19), 5123–5130 (Oct. 1, 1994).

Chae et al. (II), 8–Substituted $O^6$–Benzylguanine, Substituted 6(4)– (Benzyloxy)pyrimidine, and Related Derivatives as Inactivators of Human $O^6$–Alky;guanine–DNA Alkyltransferase, *J. Medicinal Chemistry,* 38(2), 359–365 (1995).

Friedman et al., "Activity of Temozolomide in the Treatment of Central Nervous System Tumor Xenografts," *Cancer Res.,* 55, 2853–2857 (Jul. 1, 1995).

Dolan et al. (IV), "Effect of $O^6$–Alkylguanine Pretreatment on the Sensitivity of Human Colon Tumor Cells to the Cytotoxic Effects of Chloroethylating Agents," *Cancer Res.,* 46, 4500–4504 (Sep. 1986).

Dolan et al. (V), "Depletion of $O^6$–Alkylguanine–DNA Alkyltransferase Activity in Mammalian Tissues and Human Tumor Xenografts in Nude Mice by Treatment with $O^6$–Methylguanine," *Cancer Chemotherapy and Pharmacology,* 25, 103–108 (1989).

Pegg et al., (I) "Mechanism of Inactivation of Human $O^6$–Alkylguanine–DNA Alkyltransferase by $O^6$–Benzylguanine," *Biochemistry,* 32(45), 11998–12006 (1993).

Arris et al., "Probing the Active Site and Mechanism of Action of $O^6$–Alkylguanine–DNA Alkyltransferase with Substrate Analogues ($O^6$–Substituted Guanines)," *Anti–Cancer Drug Design,* 9, 401–408 (1994).

Marathi et al., "Anti–Neoplastic Activity of Sequenced Administration of )6– Benzylguanine, Streptozocin, and 1, 3–Bis(2–chloroethyl)–1–nitrosourea In Vitro and In Vivo," *Biochemical Pharmacology,* 48(11), 2127–2134 (1994).

Wibley et al., "A Homology Model of the Three–Dimensional Structure of Human $O^6$–Alkylguanine–DNA Alkyltransferase Based on the Crystal Structure of the C–terminal Domain of the Ada Protein from *Escherichia coli,*," *Anti–Cancer Drug Design,* 10, 75–95 (1995).

Pegg et al., (II), "Increased Killing of Prostate, Breast, Colon, and Lung Tumor Cells by the Combination of Inactivators of $O^6$–Alkylguanine–DNA Alkyltransferase and N, N'–Bis(2–chloroethyl)–N–nitrosourea," *Biochemical Pharmacology,* 50(8), 1141–1148 (1995).

Berg et al., "Plasma and Cerebrospinal Fluid Pharmacokinetics of $O^6$–Benzylguanine and Time Course of Peripheral Blood Mononuclear Cell $O^6$–Alkylguanine–DNA Alkyltransferase Inhibition in the Nonhuman Primate," *Cancer Res.,* 55, 4606–4610 (Oct. 15, 1995).

PYRIMIDINE AND PURINE DERIVATIVES AND THEIR USE IN TREATING TUMOUR CELLS

CROSS REFERENCE TO RELATED APPLICATIONS

This is a continuation-in-part of application Ser. No. 08/568,576 entitled "$O^6$-subsituted guanine derivatives, a process for their preparation and their use in treating tumour cells" filed 7 Dec. 1995 which in turn is a continuation-in-part of International Application PCT/IE94/00031, with an international filing date of 8 Jun. 1994.

TECHNICAL FIELD

The present invention relates to 6-hetarylalkyloxy pyrimidine derivatives, a process for their preparation and their use in treating tumour cells. In particular, it relates to pyrimidine derivatives having hetarylalkyloxy substituents in the 6-position, these compounds exhibiting the ability to deplete $\underline{O}^6$-alkylguanine-DNA alkyltransferase (ATase) activity in tumour cells.

BACKGROUND ART

It has been suggested to use $\underline{O}^6$-alkyl guanine derivatives possessing $O^6$-alkylguanine-DNA alkyltransferase depleting activity in order to enhance the effectiveness of chemotherapeutic alkylating agents used for killing tumour cells. There is increasing evidence that in mammalian cells the toxic and mutagenic effects of alkylating agents are to a large extent a consequence of alkylation at the $\underline{O}^6$-position of guanine in DNA. The repair of $\underline{O}^6$-alkylguanine is mediated by ATase, a repair protein that acts on the $\underline{O}^6$-alkylated guanine residues by stoichiometric transfer of the alkyl group to a cysteine residue at the active site of the repair protein in an autoinactivating process. The importance of ATase in protecting cells against the biological effects of alkylating agents has been most clearly demonstrated by the transfer and expression of cloned ATase genes or cDNAs into ATase deficient cells; this confers resistance to a variety of agents, principally those that methylate or chloroethylate DNA. Whilst the mechanism of cell killing by $\underline{O}^6$-methylguanine in ATase deficient cells is not yet clear, killing by $\underline{O}^6$-chloroethylguanine occurs through DNA interstrand crosslink formation to a cytosine residue on the opposite strand via a cyclic ethanoguanine intermediate, a process that is prevented by ATase-mediated chloroethyl group removal or complex formation.

The use of $\underline{O}^6$-methylguanine and $\underline{O}^6$-n-butylguanine for depleting ATase activity has been investigated (Dolan et al., *Cancer Res.,* (1986) 46, pp. 4500; Dolan et al., *Cancer Chemother. Pharmacol.,* (1989) 25. pp 103. $\underline{O}^6$-benzylguanine derivatives have been proposed for depleting ATase activity in order to render ATase expressing cells more susceptible to the cytotoxic effects of chloroethylating agents (Moschel et al., *J. Med.Chem.,* 1992, 35, 4486). U.S. Pat. No. 5,091,430 and International Patent Application No. WO 91/13898 Moschel et al. disclose a method for depleting levels of $\underline{O}^6$-alkylguanine-DNA alkyltransferase in tumour cells in a host which comprises administering to the host an effective amount of a composition containing $\underline{O}^6$-benzylated guanine derivatives of the following formula:

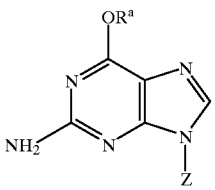

wherein Z is hydrogen, or

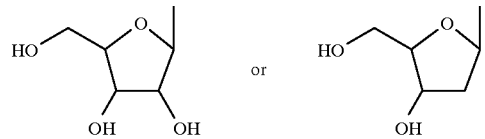

and $R^a$ is a benzyl group or a substituted benzyl group. A benzyl group may be substituted at the ortho, meta or para position with a substituent group such as halogen, nitro, aryl such as phenyl or substituted phenyl, alkyl of 1–4 carbon atoms, alkoxy of 1–4 carbon atoms, alkenyl of up to 4 carbon atoms, alkynyl of up to 4 carbon atoms, amino, monoalkylamino, dialkylamino, trifluoromethyl, hydroxy, hydroxymethyl, and $SO_nR^b$ wherein n is 0, 1, 2 or 3 and $R^b$ is hydrogen, alkyl of 1–4 carbon atoms or aryl. Mi-Young Chae et al, *J.Med.Chem.,* 1994, 37, 342–347 describes tests on $\underline{O}^6$-benzylguanine analogs bearing increasingly bulky substituent groups on the benzene ring or at position 9. Mi-Young Chae et. al., *J. Med. Chem.* 1995, 38, 359–365 published on 20 Jan. 1995 describe several 8-substituted $\underline{O}^6$-benzylguanines, 2- and/or 8-substituted 6-(benzyloxy) purines, substituted 6(4)-(benzyloxy)pyrimidines, and a 6-(benzyloxy)-s-triazine which were tested for their ability to inactivate ATase. Two types of compounds were identified as being significantly more effective than $\underline{O}^6$-benzylguanine at activating ATase in human HT29 colon tumour cell extracts. These were 8-substituted $\underline{O}^6$-benzylguanines bearing electron-withdrawing groups at the 8-position (e.g. 8-aza-$\underline{O}^6$-benzylguanine and $\underline{O}^6$-benzyl-8-bromoguanine) and 5-substituted 2,4-diamino-6-(benzyloxy)pyrimidines bearing electron withdrawing groups at the 5-position (e.g. 2,4-diamino 6-(benzyloxy)-5-nitroso- and 2,4-diamino-6-(benzyloxy)-5-nitropyrimidine). The latter derivatives were also more effective than $\underline{O}^6$-benzylguanine at inactivating ATase in intact HT29 colon tumour cells.

The present inventors are also inventors in U.S. patent application Ser. No. 08/568,576, entitled "$\underline{O}^6$-substituted guanine derivatives, a process for their preparation and use thereof in treating tumour cells" filed 7 Dec. 1995 as a Continuation-In-Part of International Application PCT/IE94/00031 which has an international filing date of 8 Jun. 1994 and which was published under No. WO 94/29312 on 22 Dec. 1994. The U.S. Application and WO 94/29312 (the contents of which are incorporated herein by reference in their entirety) describe $\underline{O}^6$-substituted guanine derivatives of formula I:

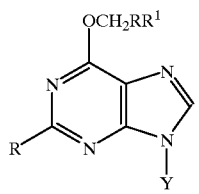

I wherein

Y is H, ribosyl, deoxyribosyl, or R"XCHR'", wherein X is O or S, R" and R'" are alkyl, or substituted derivatives thereof;

R' is H, alkyl or hydroxyalkyl;

R is (i) a cyclic group having at least one 5- or 6-membered heterocyclic ring, optionally with a carbocyclic or heterocyclic ring fused thereto, the or each heterocyclic ring having at least one hetero atom chosen from O, N, or S, or a substituted derivative thereof; or (ii) naphthyl or a substituted derivative thereof;

and pharmaceutically acceptable salts thereof.

It is an object of the present invention to provide novel compounds useful for depleting ATase activity in order to enhance the effects of chemotherapeutic agents such as chloroethylating or methylating anti-tumour agents. It is a further object to provide compounds having better ATase inactivating characteristics than $\underline{O}^6$-benzylguanine and having different solubility patterns.

Another object of the invention is to provide pharmaceutical compositions containing compounds which are useful for depleting ATase activity. A further object of the present invention is to provide a method for depleting ATase activity in tumour cells. A still further object of the invention is to provide a method for treating tumour cells in a host.

The present invention provides 6-hetarylalkyloxy pyrimidine derivatives of formula II

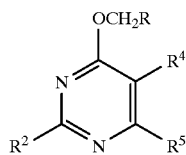

II wherein

R is as defined in (i) above, or R is phenyl or a substituted derivative thereof, $R^2$ is selected from H, $C_1$–$C_5$ alkyl, halogen or $NH_2$, $R^4$ and $R^5$ which are the same or different are selected from H, $NH_2$ or $NO_n$ where n 1 or 2, or $R^4$ and $R^5$ together with the pyrimidine ring form a 5- or 6-membered ring structure containing one or more hetero atoms, and pharmaceutically acceptable salts thereof, provided that $R^2$ is not $NH_2$ if $R^4$ and $R^5$ form a ring structure IX

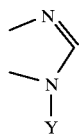

IX wherein Y is H, ribosyl, deoxyribosyl, arabinosyl, or R"XCHR'" wherein X is O or S, R"" and R'" are alkyl, or subsituted derivatives thereof, and provided that R is not phenyl;

a) if $R^2$ and $R^5$ are $NH_2$ and $R^4$ is NO or $NO_2$ b) if $R^2$ is $NH_2$ and $R^4$ and $R^5$ form a ring structure X

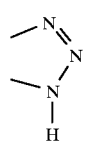

X c) if $R^2$ is $NH_2$ and $R^4$ and $R^5$ for a ring structure XI

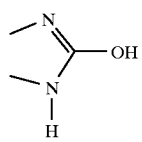

XI d) if $R^2$ is $NH_2$, $R^4$ is $NO_2$ and $R^5$ is H or $CH_3$ e) if $R^2$, $R^4$ and $R^5$ are $NH_2$.

f) if $R^2$ and $R^5$ are $NH_2$ and $R^4$ is H g) if $R^2$ is H, $R^4$ is $NO_2$ and $R^5$ is $NH_2$ h) if $R^2$ is F or OH, and $R^4$ and $R^5$ form a ring structure XII

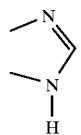

XII

R may suitably be a 5- or 6-membered heterocyclic ring or a benzo derivative thereof, in which latter case the 6-alkyloxypyrimidine moiety may be attached to R at either the heterocyclic or the benzene ring.

In preferred embodiments, R is a 5-membered ring containing S or O, with or without a second ring fused thereto.

Preferably, R is a heterocyclic ring having at least one S atom; more preferably, R is a 5-membered heterocyclic ring having at least one S atom; and most preferably, R is a thiophene ring or a substituted derivative thereof.

Alternatively, R may be a heterocyclic ring having at least one O atom, particularly, a 5-membered heterocyclic ring having at least one O atom and more particularly R may be a furan ring or a substituted derivative thereof.

As another alternative, R may be a heterocyclic ring having at least one N atom, particularly R may be a 6-membered heterocyclic ring having at least one N atom and in particular, R may be a pyridine ring.

In the definition of Y, the term "substituted derivative" includes substitution by one or more of the following groups: hydroxy, halo, alkoxy, amino, alkylamino, amido or ureido.

In the definition of R, the term "substituted derivative" includes substitution of the heterocyclic rings and/or carbocyclic ring(s) by one or more of the following groups: alkyl, alkenyl, alkynyl, halo, haloalkyl, nitro, cyano, hydroxyalkyl, $SO_nR''''$ where $R''''$ is alkyl and n=0,1 or 2, or a carboxyl or ester group of the formula —$COOR^5$ wherein $R^5$ is H or alkyl. Halo, haloalkyl, cyano, alkylenedioxy $SO_nR''''$ (as defined above) and —$COOR^5$ wherein $R^5$ is alkyl are preferred substituents.

An alkyl, alkenyl, or alkynyl group preferably contains from 1 to 20, more preferably from 1 to 10 and most preferably from 1 to 5 carbon atoms. Halo includes iodo, bromo, chloro or fluoro.

One embodiment of the invention provides a pharmaceutical composition containing compounds of formula II, wherein Y, R, $R^2$, $R^4$ and $R^5$ are as defined above, or a pharmaceutically acceptable salt thereof, and a pharmaceutically acceptable excipient. Optionally the composition may also contain an alkylating agent such as a chloroethylating or methylating agent.

In a further embodiment, the present invention provides a method for depleting Abase activity in a host comprising administering to the host an effective amount of a composition containing a compound of formula II wherein Y, R, $R^2$, $R^4$ and $R^5$ are as defined above, or a pharmaceutically acceptable salt thereof, more particularly a pharmaceutical composition as defined above. This method may alternatively be defined as a method of depleting ATase mediated DNA repair activity in a host.

The invention further provides a method for treating tumour cells in a host comprising administering to the host an effective amount of a composition containing a compound of formula II wherein Y, R, $R^2$, $R^4$ and $R^5$ are as defined above or a pharmaceutically acceptable salt thereof, more particularly a pharmaceutical composition as defined above and administering to the host an effective amount of a composition containing an alkylating agent. The method may be used for treatment of neoplasms including those which are known to be sensitive to the action of alkylating agents e.g. melanoma and glioma and others whose resistance to treatment with alkylating agents alone may be overcome by the use of an inactivator according to the invention.

Subject to the provisos above the preferred compounds of the invention are those of:

Type 1
Formula III

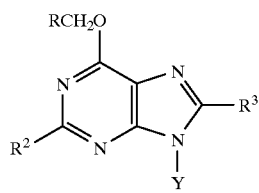

III wherein:
R is as defined for formula II, particularly furyl or thienyl unsubstituted or substituted, preferably with a halogen such as chlorine, bromine or fluorine,
Y is H or $HOCH_2CH_2OCH_2$-;
$R^2$ is H, $NH_2$, $C_1$–$C_5$ alkyl, preferably methyl, or halogen, preferably fluorine;
$R^3$ is H or OH;

Type 2
Formula IV

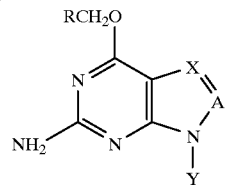

IV wherein:
R is as defined for formula II, particularly phenyl, thienyl or furyl unsubstituted or substituted preferably with a halogen such as chlorine, bromine or fluorine, or phenyl having a methylenedioxy ring structure fused thereto;
Y is as defined for formula II;
X is CH or N;
A is CH or N; and preferably when X=N, A=CH Formula V

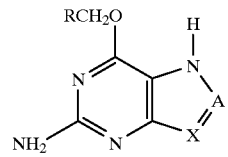

V wherein:
R is as defined for formula II
X is CH or N
A is CH or N;

Type 3
Formula VI

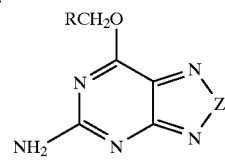

VI wherein:
R is as defined for formula II, particularly phenyl, thienyl or furyl unsubstituted or substituted preferably with a halogen such as chlorine or bromine;
Z is O or S or CH=CH;

Formula VII

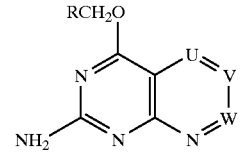

VII wherein:
R is as defined for formula II;
U is CH or N;
V is CH or N;
W is CH or N;

Type 4
Formula VIII

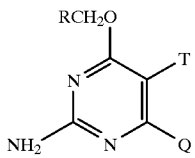

VIII wherein:

R is as defined for formula II, particularly phenyl optionally substituted with halogen preferably one or more of chlorine, fluorine or bromine, or methylenedioxy; thenyl or furyl optionally substituted with halogen preferably one or more of chlorine, bromine or fluorine;

T is H, $NH_2$ or $NO_n$ where n-=1 or 2;
Q is H, $NH_2$ or $NO_n$ where n=1 or 2;

DESCRIPTION OF THE PREFERRED EMBODIMENTS

Examples of compound of the invention are shown in Tables 1a and 1b. They were synthesized by the procedures presented below, adapted as appropriate.

Type 1

A. $O^6$-Substituted hypoxanthines were made by the action of alkoxide $RCH_2ONa$ on the quaternary salt N,N,N-trimethyl-1H-purin-6-aminium chloride.[1]

B. $O^6$-Substituted 2-methylhypoxanthines were made similarly, from the quaternary salt from diazabicyclooctane (DABCO) and 6-chloro-2-methylpurine.[2]

C. $O^6$-Substituted 2-fluorohypoxanthines were made by diazolisation of the corresponding guanines using sodium nitrite and concentrated fluoboric acid at −25° C.[3]

D. $O^6$-Substituted 9-(2-hydroxyethoxymethyl)guanines were made by condensing the corresponding guanines after silylation with 2-acetoxyethoxymethyl bromide in the presence of mercuric cyanide followed by saponificationb of the O-acetyl group.[4]

E. $O^6$-Substituted 8-hydroxyguanines were made from 6-hetarylmethyl-2,4,5-triaminopyrimidines and 1, 1-carbonyldiimidazole in DMF.[5] Reaction of 6-chloro-2,4-diaminopyrimidine with alkoxide in DMSO, followed by nitrosation with sodium nitrite in aqueous acetic acid and reduction using sodium hydrosulphite in aqueous DMF, fave the 2, 4, 5-triamines.

Type 2

$O^6$-Substituted 8-azaguanines were made from the above triamines and sodium nitrite in aqueous acetic acid.[6]

B. $O^6$-Substituted 8-aza-7-deazaguanines were made from the alkoxide $RCH_2ONa$ and 2-amino-6-chloro-8-aza-7-deazapurine[7] in sulfolane or from the DABCO quaternary salt (in DMSO solvent) derived from it.

Type 3

A. $O^6$-Substituted 8-oxaguanines were made by lead tetraacetate oxidation[8] of 6-hetarylmethyl-2,4-diamino-5-nitrosopyrimidines obtained as under Type IE.

B. $O^6$-Substituted 8-thiaguanines were made from the triamine intermediates under Type IE and N-tosylthionylimine in pyridine.[9]

C. $O^4$-Substituted pterins were made from these triamines and glyoxal with sodium metabisulphite.[10]

Type 4

A and B. These pyrimidines were obtained as under Type IE.

C. $O^6$-Substituted 2,4-diamino-5-nitropyrimidines were made by the action of alkoxide $RCH_2ONa$ in DMSO on 6-chloro-2,4-diamino-5-nitropyrimidine.[11]

Compounds of formula II in which Y is R"XCHR'". (seco-nucleosides) may be prepared by an analogous preparation to the reaction of $O^6$-benzylguanine with α-chloroethers (MacCoss et al., *Tetrahedron Lett.;* European Patent Application No. 184,473., loc. cit.) or with alkyl bromides (e.g. Kjellberg, Liljenberg and Johansson, *Tetrahedron Lett.*, 1986, 27, 877; Moschel, McDougall, Dolan, Stine, and Pegg, *J.Med. Chem.*, 1992, 35, 4486).

Typical "sugar" components corresponding to R"XCHR'", leading to seco-nucleosides, are made by methods described in e.g. McCormick and McElhinney, *J. Chem. Soc., Perkin Trans.* 1, 985, 93; Lucey, McCormick and McElhinney, *J. Chem. Soc, Perkin Trans.* 1, 1990, 795.

Compounds of formula II in which Y is ribosyl or deoxyribosyl (nucleosides) may be prepared by methods analogous to the syntheses of $O^6$-benzylguanine riboside and 2-deoxyriboside (Moschel et al. 1992; cf. Gao, Fathi, Gaffney et al., *J. Org. Chem.*, 1992, 57, 6954; Moschel, Hudgins and Dipple, *J. Amer. Chem. Soc.*, 1981, 103, 5489) (see preparation of Ribosides above).

The amount of the compound of the present invention to be used varies according to the effective amount required for treating tumour cells. A suitable dosage is that which will result in a concentration of the compound of the invention in the tumor cells to be treated which results in the depletion of ATase activity, e.g. about 1–2000 mg/kg body weight, and preferably 1–800 mg/kg body weight, particularly 1–120 mg/kg body weight, prior to chemotherapy with an alkylating agent.

The pharmaceutical composition of the invention may be formulated in conventional forms with conventional excipients, as described for example in U.S. Pat. Nos. 5,091,430 and 5,352,669, the contents of which are incorporated herein by reference in their entirety. The composition may contain the inactivator according to the invention together with an alkylating agent; or the composition may comprise two parts, one containing the inactivator and the other containing the alkylating agent. The method of administering the compounds of the invention to a host may also be a conventional method, as described in U.S. Pat. Nos. 5,091,430 and 5,352,669 for example. For administration of an inactivator according to the invention to patients, the pharmaceutical composition may suitably contain the inactivator in a suitable vehicle such as 40% polyethyleneglycol 400 in saline solution, or in saline or 3% ethanol (in saline), for intravenous injection, or in a powder form in suitable capsules for oral administration.

Alkylating agents may be administered in accordance with known techniques and in conventional forms of administration, as described in U.S. Pat. Nos. 5,091,430 and 5,352,669 for example or preferably as a single dose immediately after or up to 24 hours after but preferably around 2 hours after administration of the ATase inactivating agents and also at doses lower than those used in standard treatment regimen. A reduction in dose may be necessary because the inactivators would generally be anticipated to increase the toxicity of the alkylating agents. Examples of chloroethylating agents include 1,3 bis (2-chloroethyl)-1-nitrosourea (BCNU), 1-(2-chloroethyl)-3-cyclohexyl-1-nitrosourea (CCNU), fotemustine, mitozolomide and clomesone and those described in McCormick, McElhinney, McMurry and Maxwell *J. Chem. Soc, Perkin Trans. I*, 1991, 877 and Bibby, Double, McCormick, McElhinney, Radacic, Pratesi and Dumont *Anti-Cancer Drug Design*, 1993, 8, 115. Examples of methylating agents include temozolomide U.S. Pat. No. 5,260,291 the contents of which are incorporated herein in their entirety) and dacarbazine, procarbazine, and streptozocin.

Method of Purification of Recombinant ATases

The cDNA cloning and overexpression of the human ATase has been reported previously[23]. Purification of the recombinant proteins was achieved either by affinity chromatography through a DNA-cellulose column as described by Wilkinson et al.,[25, 26] or by DEAE-cellulose ion-exchange chromatography. For the latter, the ATase protein was partially purified by ammonium sulphate precipitation (30–60%) and dialyzed against 10 mM Tris-HCl pH 7.5, 1 mM DTT, 2 mM EDTA, 10% glycerol, before loading on a DEAE-cellulose column. The ATase was then eluted with a 0–0.1 M NaCl gradient. The purified human ATase protein retained activity for more than one year when stored at high concentration at −20° C. in buffer I [50 mM-Tris/HCl (pH 8.3)3 mM-dithiothreitol/1 mM-EDTA] and could be thawed and refrozen several times without substantial loss of activity.

Incubation with Inactivators and ATase Assay

Compounds to be tested were dissolved in DMSO to a final concentration of 10 mM and diluted just before use in buffer I containing 1 mg/ml bovine serum albumin (IBSA). Recombinant ATase was diluted in IBSA and titrated in order that the reaction be conducted under ATase, and not substrate, limiting conditions. In each assay, fixed amounts of ATase (60–75 fmol) were incubated with varying amounts of $O^6$-benzylguanine, or test compound in a total volume of 200 ul of IBSA containing 10 ug of calf thymus DNA at 37° C. for 1 hour. ATase substrate DNA was prepared by incubation of purified calf thymus DNA with N-[$^3$H]-methyl-N-nitrosourea (18.7 Ci/mmole, Amersham International). The [$^3$H]-methylated-DNA substrate (100 ul containing 6.7 ug of DNA and 100 fmol of $O^6$-methylguanine) was added and incubation continued at 37° for 1 hour, until the reaction was completed. Following acid hydrolysis of the DNA as previously described[21] the [$^3$H]-methylated protein was recovered and quantitated by liquid scintillation counting. Samples were typically assayed in duplicate and experiments repeated several times. $I_{50}$ is the concentration of inactivator required to produce a 50% reduction in ATase activity.

Test Results

The results of the AT assay are shown in Table 2. Many of the compounds tested were more efficient in inactivating ATase than $O^6$-benzylguanine. In accordance with the results in the parent application, compounds in which R is a heterocyclic group were more efficient than the comparable compounds having benzyloxy side chains. In general the compounds in which $RCH_2$ is substituted or unsubstituted thenyl were the most efficient, the most preferred being halo-substituted thenyl having its halo substituent in a 1,3-relationship with the methyleneoxy group attached to the pyrimidine residue.

Typical Synthetic Procedures

Type 1A.
$O^6$-(4-Bromothenyl)hypoxanthine. B. 4292

4-Bromothenyl alcohol (1.16 g, 6 mmol) was added to sodium hydride (60% in oil; 0.16 g, 2 mmol) and DMSO (1 ml), The solution was stirred for 30 min. The trimethylammonium salt (0.427 g, 2 mmol) was then added and stirring continued for 2.5 h at 20° C. The solution was cooled in an ice bath and poured into ether (60 ml) containing acetic acid (0.32 ml). A white precipitate was collected, triturated with water (4 ml) and collected again to give B. 4292 (436 mg, 69%) recrystallised from methanol.

Type 1B.
$O^6$-Thenyl-2-methylhypoxanthine, B. 4350
DABCO salt from 6-chloro-2-methylpurine:

6 chloro-2-methylpurine (0.5 g, 3 mmol) was dissolved in a mixture of DMF (5 ml) and diglyme (25 ml). DABCO (0.66 g, 6 mmol) was then added. The mixture was Stinfed for 1 h and the precipitate collected to give the quatenary salt (700 mg, 82%). NMR (300 MHz, DMSO-$d_6$): shift in ppm 2.65 (s), 3.27 (t, J=7.5 Hz), 3.78 (s), 4.14 (t, J=7.5 Hz), 8.21 (s).

Thenyl alcohol (684 mg, 6 mmol) was added to sodium hydride (60% in oil; 80 mg, 2 mmol) and DMSO (0.5 ml). The solution was stirred for 30 min. The DABCO salt was then added and stirring continued for 5 h. The solution was then poured into ether (30 ml) containing acetic acid (0.15 ml). A precipitate was collected, triturated with water (4 ml) and collected again to give $O^6$-Thenyl-2-methylhypoxanthine (96 mg, 35%) recrystallised from acetonitrile.

Type 1C.
$O^6$-(4-Bromothenyl)-2-fluorohypoxanthine, B. 4353

To 3.6 ml of 40% fluoroboric acid precooled to −25° C. in a bath was added $O^6$-(4-bromothenyl) guanine (326 mg, 1 mmol) with vigorous stirring. A solution of sodium nitrite (0.116 g, 1.7 mmol) in water (0.15 ml) was added dropwise over a period of 10 min. After 20 min, the solution was poured into ice. The mixture was then allowed to stand at 0° C. for 15 h, then collected and dried to afford almost pure (t.l.c.) B. 4353 (180 mg, 55%). Flash chromatography (Hexane—Ethyl Acetate decreasing polarity little by little) afforded B. 4353

Type 1D.
$O^6$-(4-Bromothenyl)-9-(2-hydroxyethoxymethyl)guanine, B. 4335

A stirred mixture of $O^6$-(4-Bromothenyl)guanine (294 mg, 1 mmol), $(NH_4)_2SO_4$ (47 mg) and hexamethyldisilazane (5 ml) was heated at reflux for 3 h. Volatile material was then evaporated under vacuum. The residue was stirred with benzene (15 ml) and $Hg(CN)_2$ (344 mg, 1.3 mmol) under reflux for 30 min. A solution of (2-acetoxyethoxy)methyl bromide (197 mg, 1 mmol) in benzene (10 ml) was added, reflux maintained for 2 h, and the cloudy solution diluted with chloroform (150 ml). The organic phase was washed with saturated aqueous $NaHCO_3$ (30 ml), followed by KI (1M; 30 ml), dried over $MgSO_4$ and evaporated to give an oil (313 mg). This oil was chromatographed on a silica gel column with $CHCl_3$-McOH (12:1) as eluant, yielding almost pure (t.l.c.) O-acetate (141 mg) of B. 4335. Methanol (60 ml) was saturated with dry ammonia and poured onto this O-acetate in a flask which was tightly stoppered. After dissolution, stirring was stopped and the flask left closed overnight. Evaporation of methanol gave B. 4335 (135 mg, 46%), recrystallised from isopropanol.

Type 1E.
O$^6$-(4-Bromothenyl)-8-hydroxyguanine, B. 4349

Sodium hydride (60% in oil; 416 mg, 10.4 mmol) was added to a stirred solution of 4-bromothenyl alcohol (2.32 g, 12 mmol) in DMSO (5 ml). After 30 min, 6-chloro-2,4-diaminopyrimidine (1.45 g, 10 mmol) was added and the solution heated for 2 h at 80° C. Solvent was removed at 45° C.–50° C./0.5 mm and the oily residue triturated with water, yielding O6-(4-bromothenyl)-2,4-diamino-6-hydroxypyrimidine (2.83 g, 94%).

To a mixture of this diamine (1.8 g, 6 mmol) in acetic acid (34 ml) and water (68 ml) was added over 20 min a solution of NaNO$_2$(0.6 g, 8.7 mmol) in water (24 ml). The purple 5-nitroso derivative (1.6 g, 81%) was filtered off and washed with water.

The 5-nitrosopyrimidine (330 mg, 1 mmol) in DMF 10 ml) was vigorously stirred at 55° C. with sodium hydrosulphite (609 mg, 3.5 mmol) and treated dropwise over 12 min with water (10 ml). Stirring was continued for 15 min longer and the solvent evaporated in vacuo. The residue was suspended in water (6 ml), the pH adjusted to 9 with ammonium hydroxide, and the product extracted with ethyl acetate. Drying and evaporation yielded O$^6$-(4-bromothenyl)-2,4,5-triamino-6-hydroxypyrimidine (267 mg, 85%) as a yellow solid.

The triamine (250 mg, 0.79 mmol) in DMF (1 ml) was treated with 1,1'-carbonyldiimidazole (162 mg, 1 mmol) under argon and the solution left for 24 h. Dilution with water yielded the product B. 4349 (226 mg, single spot on t.l.c.), which was dissolved in 2 M NaOH (30 ml), clarified by filtration, and reprecipitated by acetic acid, Recrystallisation yielded 138 mg (56%).

Type 2A.
O$^6$-(4-Chlorothenyl)-8-azaguanine, B. 4314

O$^6$-(4-Chlorothenyl)-2,4-diamino-5-nitroso-6-hydroxypyrimidine (286 mg, 1 mmol) was reduced by sodium hydrosulphite as a Type 1E and the triamine obtained dissolved in acetic acid (3 ml) and water (15 ml) at 0° C. NaNO$_2$ (75 mg, 1.1 mmol) in water (1.2 ml) was added dropwise and, after stirring for 1 hour the precipitate (150 mg) was collected and washed with water and recrystallised.

Type 2B.
O$^6$-Thenyl-6-aza-7-deazaguanine, B. 4338

Sodium hydride (60% in oil; 80 mg, 2 mmol) was added to a solution of thenyl alcohol (342 mg, 3 mmol) in sulfolane (9 ml) with stirring and set aside for 30 minutes. 6-Chloro-8-aza-7-deazaguanine (170 mg, 1 mmol) in sulfolane (5 ml) was added and the reaction mixture heated at 65° C. for 2 hours. The mixture was then cooled and added to a solution of acetic acid (0.12 ml) in ether (100 ml). After 1 hour the sodium chloride was filtered off and the ether evaporated. The sulfolane was removed under reduced pressure (90° C. at 0.5 mmHg) and the residue washed with water and extracted with ethanol, yielding B. 4338 (168 mg, 68%) O$^6$-(4-chlorobenzyl)-8-aza-7-deazaguanine, B. 4339

DABCO (278 mg, 2.48 mmol) was added to a solution of 6-chloro-8-aza-7-deazaguanine (210 mg, 1.24 mmol) in DMF (3 ml) and the mixture stirred at room temperature for 1 hour. The precipitate of quaternary salt (260 mg, 75%) was removed by filtration and washed with acetone. Sodium hydride ( 60% in oil; 52 mg, 1.3 mmol) was added to a stirred solution of 4-chlorobenzyl alcohol (278 mg,1.95 mmol) in DMSO (2 ml) and the mixture stirred for 30 minutes. The quaternary salt (180 mg, 0.65 mmol) was added and after stirring at room temperature for 6 hours, the insoluble material was filtered off and treated with water (30 ml). The product B. 4339 (162 mg, 92%) was filtered off and dried.

Type 3A.
O$^6$-(4-fluorobenzyl)-8-oxaguanine, B. 4272

O$^6$-(4fluorobenzyl)-2,4diamino5-nitroso-hydroxypyrimidine (263 mg.1 mmol), prepared as in type IE, was suspended in acetic acid (4 ml). Lead tetraacetate (85%, 57 mg, 1.1 mmol) was added in portions with stirring over 10 minutes under nitrogen. After 1.5 hours the product (191 mg) was collected and dried. Recrystallisation from acetone yielded pure B. 4272.

Type 3B.
O$^6$-(4-Bromothenyl)-8-Thiaguanine, B. 4351

A solution of O$^6$-(4-bromothenyl)-2,4,5-triamino-6-hydroxypyrimidine (474 mg, 1.5 mmol), as prepared in Type 1E, and N-tosylthionylimine (652 mg, 3 mmol) in dry pyridine (15 ml) was stirred, under a nitrogen atmosphere, for 2h. The pyridine was removed in vacuo and successive amounts of EtOH were added and removed until a yellow solid was obtained. Crystallisation from methanol gave B 4351 (212 mg).

Type 3C.
O$^4$-(4-Bromothenyl)pterin, B. 4288

A solution of glyoxal trimer (84 mg, 1.2 mmol) and sodium metabisulphite (228 mg, 1.2 mmol) in water (4 ml) at 80° C. was added in one portion to a refluxing solution of O$^6$-(4-bromothenyl)-2,4,5-triamino-6-hydroxypyrimidine (316 mg, 1 mmol), prepared as in type 1E. The mixture was allowed to reach room temperature and the pH adjusted to 9. The solid (213 mg) was collected, dried and recrystallised from methanol to give B. 4288 (112 mg, 33%).

Type 4A.
O$^6$-(4-Chlorothenyl)-2,4-diamino-6-hydroxypyrimidine, B.4302

Sodium hydride (60% in oil; 624 mg, 15.6 mmol) was added to a stirred solution of 4-chlorothenyl alcohol (2.7 g, 18 mmol) in DMSO (7.5 ml). After 30 min, 6-chloro-2,4-diaminopyrimidine (2.17 g, 15 mmol) was added and the solution heated for 2 h at 80° C. The solvent was removed in vacuo and the oily residue was triturated with water, yielding B.4302 (3.6 g).

Type 4B.
O$^6$-(4-Chlorothenyl)-2,4-diamino-6-hydroxy-5-nitrosopyrimidine, B.4311

To a stirred solution of O$^6$-(4-chlorothenyl)-2,4-diamino-6-hydroxyprimidine (257 mg, 1 mmol), prepared as Type 4A, in acetic acid (5.4 ml) and water (12.6 ml), was added a solution of NaNO$_2$ (100 mg, 1.45 mmol) in water (4 ml). The purple precipitate of B. 4311 (240 mg, single spot on t.l.c.) was collected and dried.

Type 4C.
O$^6$-(4-Piperonyl)-2,4-diamino-6-hydroxy-5-nitropyrimidine, B.4308

Sodium hydride (60% in oil; 440 mg, 11 mmol) was added to a stirred solution of piperonyl alcohol (3.1 g, 20 mmol) in DMSO (5 ml). After 30 min, 2,4-diamino-6-chloro-5-nitropyrimidine (1.9 g, 10 mmol) was added and the mixture was stirred under argon for 3.5 h. Acetic acid (1 ml) in ether (300 ml) was added to the cooled mixture. Trituration with ether gave an oily solid (2.0 g) which was washed with water and dried. Recrystallisation from DMF gave B. 4308.

Type 5.
S⁶-(4-Bromothenyl)-6-thioguanine, B.4352

Sodium hydride (60% in oil; 44 mg, 1.1 mmol) was added to a solution of 4-bromothenyl mercaptan (418 mg, 2 mmol) in DMSO (0.5 ml). After 30 min, 2-amino-N,N,N-trimethyl-1H-purin-6-aminium chloride (228 mg, 1 mmol) was added and stirring continued 1 h. Acetic acid (0.12 ml) and ether (30 ml) were added and after decantation and trituration with fresh ether, B.4352 (38 mg, 11%) was filtered off.

TABLE Ia

| Compound, Test No. | O⁶-Substituent RCH₂ | Yield % | Solvent for Recrystn. | M.p. (decomp.) (° C.) | Formula | Molecular Weight | | Analysis C | H | N |
|---|---|---|---|---|---|---|---|---|---|---|
| Type 1A. Hypoxoathines | | | | | | | | | | |
| B. 4293 | furfuryl | 60 | MeOH | 154 | $C_{10}H_8N_4O_2$ | 216 | | | | |
| B. 4291 | theonly | 66 | MeOH | 168 | $C_{10}H_8N_4OS$ | 232 | Found | 51.85 | 3.43 | 24.12 |
| | | | | | | | Req. | 51.71 | 3.47 | 24.12 |
| B. 4292 | 4-bromothenyl | 69 | MeOH | 170 | $C_{10}H_7BrN_4OS$ | 311 | Found | 38.33 | 2.18 | 17.66 |
| | | | | | | | Req | 38.6 | 2.26 | 18.00 |
| 1B. 2-Methylhypoxanthines | | | | | | | | | | |
| B. 4347 | benzyl | 43 | MeCN | 191–193ᵃ | $C_{13}H_{12}N_4O$ | 240 | Found | 65.05 | 4.91 | 23.30 |
| | | | | | | | Req | 64.99 | 5.03 | 23.32 |
| B. 435C | thenyl | 35 | MeCN | 176–178ᵃ | $C_{11}H_{10}N_4OS$ | 325 | Found | 53.63 | 3.90 | 22.67 |
| | | | | | | | Req | 53.64 | 4.09 | 22.75 |
| 1C. 2-Fluorohypoxanthines | | | | | | | | | | |
| B. 4353 | 4-bromothenyl | 55 | Column | 142 | $C_{10}H_6BrFN_4OS$ | 329 | | | | |
| 1D. 9-(2-Hydroxyethoxy-methyl)guaniaes | | | | | | | | | | |
| B. 4334 | benzyl | 45 | i-PrOH | 150–152ᵃ | $C_{15}H_{17}N_5O_3$ | 315 | Found | 57.19 | 5.59 | 21.93 |
| | | | | | | | Req | 57.13 | 5.43 | 22.21 |
| B. 4335 | 4-bromothenyl | 42 | i-PrOH | 156–158ᵃ | $C_{13}H_{14}BrN_5O_3S$ | 40C | Found | 39.16 | 3.68 | 17.20 |
| | | | | | | | Req | 39.01 | 3.53 | 17.50 |
| 1E. 8-Hydroxyguannines | | | | | | | | | | |
| B. 4349 | 4-bromothenyl | 56 | Aq. EtOH | >230 | $C_{10}H_6BrN_5O_2S \cdot \frac{1}{2}H_2O$ | 351 | Found | 34.53 | 2.48 | 19.50 |
| | | | | | | | Req. | 34.20 | 2.58 | 19.94 |
| Type 2A. 8-Aragucanines | | | | | | | | | | |
| B. 4270 | 4-fluorobenzyl | 40 | Aq. MeOH | >280 | $C_{11}H_9FN_6O$ | 260 | Found | 51.50 | 3.85 | 29.44 |
| | | | | | | | Req. | 50.77 | 3.49 | 32.30 |
| B. 4314 | 4-chlorothenyl | 26 | Aq. MeOH | >200 | $C_9H_7ClN_6OS$ | 282.7 | Found | 38.86 | 2.61 | 28.61 |
| | | | | | | | Req. | 38.24 | 2.50 | 29.73 |
| B. 4289 | 4-bromothenyl | 12 | MeCN | >190 | $C_9H_7BrN_6OS$ | 327 | Found | 35.91 | 2.78 | 24.60 |
| 2B. 8-Aza-7-dezazguonines | | | | | | | | | | |
| B. 4310 | benzyl | | MeOH | 160 | $C_{12}H_{11}N_5O \cdot H_2O$ ½H₂O.¼EtOH | 259 | Found | 55.53 | 4.9 | 26.41 |
| | | | | | | | Req. | 55.59 | 5.01 | 27.02 |
| B. 4340 | 4-fluorobenzyl | 65 | EtOH | 188 | $C_{12}H_{10}FN_5O \cdot ¼H_2O$ ½H₂O.¼EtOH | 263.7 | Found | 53.82 | 3.76 | 26.97 |
| | | | | | | | Req. | 54.6 | 4.0 | 26.55 |
| B. 4339 | 4-chlorobenzyl | 92 | EtOH | 242–244ᵃ | $C_{12}H_{10}ClN_5O \cdot$ ½H₂O.¼EtOH | 296 | Found | 51.15 | 3.89 | 23.43 |
| | | | | | | | Req. | 50.7 | 4.25 | 23.64 |
| B. 4343 | piperonyl | 50 | EtOH | 186 | | | | | | |
| B. 4348 | furfuryl | | EtOH | 150ᵃ | $C_{13}N_{18}N_5O_3$ | 285 | Found | 54.52 | 3.82 | 24.50 |
| | | | | | | | Req. | 54.7 | 3.88 | 24.55 |
| B. 4338 | thenyl | 68 | EtOH | 180 | $C_{10}H_9N_5O_2 \cdot ¼H_2O$ | 235.7 | Found | 50.96 | 3.87 | 29.54 |
| | | | | | | | Req. | 50.96 | 4.06 | 29.71 |
| B. 4337 | 4-bromothenyl | 79 | EtOH | 180 | $C_{10}H_9N_5OS$ | 247 | Found | 47.58 | 3.54 | 27.41 |
| | | | | | | | Req. | 47.7 | 3.8 | 27.8 |
| | | | | | $C_{10}H_8BrN_5OS$ | 326 | Found | 37.08 | 2.51 | 21.31 |
| | | | | | | | Req. | 36.8 | 2.5 | 21.5 |
| Type 3A. 8-Oxaguanines | | | | | | | | | | |
| B. 4272 | 4-fluorobenzyl | 41 | Acetone | 223–224 | $C_{11}H_8FN_5O_2$ | 261 | Found | 50.89 | 3.08 | 26.65 |
| | | | | | | | Req. | 50.58 | 3.09 | 26.81 |
| B. 4285 | 4-chlorobenzyl | 63 | Acetone | 219–220 | $C_{11}H_8ClN_5O_2$ | 277.7 | Found | 47.59 | 2.88 | 25.25 |
| | | | | | | | Req. | 47.58 | 2.90 | 25.22 |
| B. 4299 | 4-chlorothenyl | 55 | Acetone | 164–165 | $C_9H_6ClN_5O_2S$ | 283.7 | Found | 37.68 | 2.15 | 24.43 |
| | | | | | | | Req. | 38.10 | 2.19 | 24.69 |
| B. 4287 | 4-bromothenyl | 61 | Acetone | 170–172 | $C_9H_6BrN_5O_2S$ | 328 | Found | 33.30 | 1.85 | 21.37 |
| | | | | | | | Req. | 32.94 | 1.84 | 21.34 |
| 3B. 8-Thlaguanines | | | | | | | | | | |
| B. 4296 | benzyl | 39 | EtOH | | $C_{11}H_9N_5OS$ | 259 | | | | |
| B. 4286 | 4-fluorobenzyl | 11 | PLC | | $C_{11}H_8FN_5OS$ | 277 | | | | |
| B. 4315 | 4-chlorothenyl | 13 | MeOH | | $C_9H_6ClN_5OS_2$ | 299.8 | Found | 36.27 | 2.04 | 23.07 |
| | | | | | | | Req. | 36.06 | 2.02 | 23.36 |

TABLE Ia-continued

| Compound, Test No. | O⁶-Substituent RCH₂ | Yield % | Solvent for Recrystn. | M.p. (decomp.) (° C.) | Formula | Molecular Weight | Analysis | C | H | N |
|---|---|---|---|---|---|---|---|---|---|---|
| B. 4351 | 4-bromothenyl | 41 | MeOH | 156–160 | $C_9H_6BrN_5OS_2$ | 344 | Found | 31.49 | 1.60 | 20.11 |
|  |  |  |  |  |  |  | Req. | 31.41 | 1.76 | 20.35 |
| 3C. Pterins (O⁴-substituent) |  |  |  |  |  |  |  |  |  |  |
| B. 4290 | 4-flurobenzyl | 55 | MeOH | >210 | $C_{13}H_{10}FN_5O$ | 271 | Found | 57.87 | 3.88 | 25.65 |
|  |  |  |  |  |  |  | Req. | 57.56 | 3.72 | 25.82 |
| B. 4316 | 4-chlorothenyl | 41 | MeOH | >170 | $C_{11}H_8ClN_5OS$ | 293.7 | Found | 44.93 | 2.84 | 23.72 |
|  |  |  |  |  |  |  | Req. | 44.98 | 2.75 | 23.84 |
| B. 4288 | 4-bromothenyl | 63 | MeOH | 178–179 | $C_{11}H_8BrN_5OS$ | 338 | Found | 39.34 | 3.13 | 20.25 |
|  |  |  |  |  |  |  | Req. | 39.07 | 2.38 | 20.71 |
| Type 4A. 2,4-diamino-6-hydroxypyrimidines |  |  |  |  |  |  |  |  |  |  |
| B. 4305 | 4-fluorobenzyl | 98 | $C_6H_6$/Petrol | 133–134 | $C_{11}H_{13}FN_4O$ | 234 | Found | 56.20 | 4.79 | 23.66 |
|  |  |  |  |  |  |  | Req. | 56.40 | 4.73 | 23.92 |
| B. 4304 | 4-chlorobenzyl | 31 | $C_6H_6$ | 122–123 | $C_{11}H_{13}ClN_4O$ | 250.7 | Found | 52.43 | 4.56 | 22.47 |
|  |  |  |  |  |  |  | Req. | 52.70 | 4.42 | 22.35 |
| B. 4303 | piperonyl | 79 | MeCN | 168–171 | $C_{12}H_{12}N_4O_3$ | 260 | Found | 55.31 | 4.64 | 21.38 |
|  |  |  |  |  |  |  | Req. | 55.38 | 4.65 | 21.52 |
| B. 4307 | thenyl | 97 | MePh | 100 | $C_9H_{10}N_4OS$ | 222 | Found | 48.83 | 4.58 | 25.25 |
|  |  |  |  |  |  |  | Req. | 48.63 | 4.54 | 25.21 |
| B. 4302 | 4-chlorothenyl | 45 | MePh | 129–130 | $C_9H_9ClN_4OS$ | 256.7 | Found | 42.40 | 3.68 | 22.00 |
|  |  |  |  |  |  |  | Req. | 42.11 | 3.53 | 21.83 |
| 4B. 2,4-Diamino-6-hydroxy-5-nitrosopyrimidines |  |  |  |  |  |  |  |  |  |  |
| B. 4301 | 4-fluorobenzyl | 76 | MeOH | >250 | $C_{11}H_{10}FN_5O_2$ | 263 | Found | 49.60 | 3.90 | 26.29 |
|  |  |  |  |  |  |  | Req. | 50.19 | 3.83 | 26.61 |
| B. 4311 | 4-chlorothenyl | 84 | Acetone | >190 | $C_9H_8ClN_5O_2S$ | 285.7 | Found | 37.54 | 2.79 | 24.22 |
|  |  |  |  |  |  |  | Req. | 37.84 | 2.82 | 24.51 |
| B. 4312 | 4-bromothenyl | 62 | Acetone | 200–201 | $C_9H_3BrN_3O_2S$ | 330 | Found | 32.87 | 2.38 | 20.95 |
|  |  |  |  |  |  |  | Req. | 32.74 | 2.44 | 21.21 |
| 4C. 2,4-Diamino-6-hydroxy-5-nitropyrlaudines |  |  |  |  |  |  |  |  |  |  |
| B. 4308 | piperonyl | 67 | DMF | >175 | $C_{12}H_{11}N_5O_5$ | 365 | Found | 47.44 | 4.07 | 22.83 |
|  |  |  |  |  |  |  | Req. | 47.22 | 3.63 | 22.94 |
| B. 4306 | thenyl | 34 | MeOH | 159–160 | $C_9H_9N_5O_2S$ | 267 | Found | 40.99 | 3.71 | 25.99 |
|  |  |  |  |  |  |  | Req. | 40.44 | 3.39 | 26.21 |

[a]Without decomposition

TABLE Ib

| Compound Type, Test No. | O⁶-Substituent RCH₂ | $\lambda_{min}$ (MeOH) (nm) | $\delta_H$/ppm from TMS, $(CD_3)_2SO$, /J(Hz) |
|---|---|---|---|
| Type 1A. Hypoxanthines |  |  |  |
| B. 4293 | furfuryl | 252 | 5.60(s), 6.53(dd, 3.1, 1.9), 6.69(d, 3.1), 7.76(dd, 1.9, 0.9) 8.39(s), 8.55(s) |
| B. 4291 | thenyl | 240 | 5.63(s), 7.08(dd, 5.1, 3.4), 7.35(d, 3.4), 7.6(d, 5.1), 8.39(s), 8.51(s) |
| B. 4292 | 4-bromothenyl | 251 | 5.80(s), 7.38(d, 1.3), 7.73(d, 1.3), 8.42(s), 8.58(s) |
| Type 1B. 2-Methyltypoxanthines |  |  |  |
| B. 4347 | benzyl | 256 | 2.61(s), 5.60(s), 7.50(m), 8.32(s) |
| B. 4350 | thenyl | 240 | 2.63(s), 5.77(s), 7.05(dd, 5.1, 2.4, 7.33(d, 2.4), 7.58(dd, 5.1, 1.0) 8.25(s), 13.22(s) |
| Type 1C. 2-Fluorohypoxanthines |  |  |  |
| B. 4353 | 4-bromothenyl | 233, 255 | 5.77(s), 7.4(d, 1.5), 7.77(d, 1.5), 8.45(s), 13.64(bs). |
| Type 1D. 9-(2-Hydroxyethoxymethyl,guanines |  |  |  |
| B. 4334 | benzyl | 247, 283 | 3.48(m), 4.70(s), 5.45(s), 6.59(s), 7.45(m), 8.03(s), |
| B. 4335 | 4-bromothenyl | 245, 284 | 3.49(m), 4.71(s), 5.45(s), 5.56(s), 6.65(s), 7.30(d, 1.5) 7.72(d, 1.5) 8.04(s) |
| Type 1E. 8-Hydroxyguanines |  |  |  |
| B. 4349 | 4-bromothenyl | 239, 293 | 5.54(s), 6.24(s), 7.33(d, 1.4) 7.70(d, 1.4), 10.49(s) 11.12(s) |
| Type 2A. 8-Azaguanines |  |  |  |
| B. 4270 | 4-fluorobenzyl | 288 | 5.57(s), 7.04(s), 7.28(m), 7.65(m), 15.38(s). |
| B. 4314 | 4-chlorothenyl | 288 | 5.71(s), 7.13(s), 7.41(d, 1.5), 7.66(d, 1.5), 15.42(s). |
| B. 4289 | 4-bromothenyl | 287 | 5.73(s), 7.12(s), 7.43(d, 1.5), 7.76(d, 1.5), 15.39(s). |
| Type 2B. 8-Aza-7-deazaguanines |  |  |  |
| B. 4310 | benzyl | 277 | 5.50(s), 6.68(s), 7.74(m), 7.82(s), 12.87(bs) |
| B. 4340 | 4-fluorobenzyl | 278 | 5.49(s), 6.70(s), 7.20(m), 7.61(m), 7.82(s), 12.88(bs) |

TABLE Ib-continued

| Compound Type, Test No. | O⁶-Substituent RCH₂ | $\lambda_{min}$ (MeOH) (nm) | $\delta_H$/ppm from TMS, (CD₃)₂SO, /J(Hz) |
|---|---|---|---|
| B. 4339 | 4-chlorobenzyl | 276 | 5.50(s), 6.69(s), 7.49(d, 8.4), 7.56(d, 8.4), 7,83(s) 12.90(s). |
| B. 4343 | piperonyl | 282 | 5.39(s), 6.05(s), 6.69(s), 6.94(d, 7.9) 7.04(dd, 7.9, 1.5), 7.14(d, 1.5), 7.80( 12.86(bs). |
| B. 4348 | furfuryl | 277 | 5.46(s), 6.52(s), 6.70(s), 6.71(s), 7.73(s), 7.79(s), 12.85(bs). |
| B. 4338 | thenyl | 278 | 5.69(s), 6.73(s), 7.07(d, 3.5), 7.35(s), 7.60(d, 1.1), 7.79(s), 12.90(bs). |
| B. 4337 | 4-bromothenyl | 278 | 5.65(s), 6.76(s), 7.38(d, 1.3), 7.72(d, 1.3), 7.81(s), 12.91(bs). |
| Type 3A. 8-Oxaguanines | | | |
| B. 4272 | 4-fluorobenzyl | 257, 341 | 5.62(s), 7.30(t, 9.1), 7.68(m), 7.91(s), 7.97(s). |
| B. 4285 | 4-chlorobenzyl | 256, 340 | 5.63(s), 7.53(d, 8.3), 7.65(d, 8.3), 7.90(s), 7.97(s). |
| B. 4299 | 4-chlorothenyl | 252, 343 | 5.78(s), 7.46(d, 1.6), 7.72(d, 1.6), 7.95(s), 8.01(s). |
| B. 4287 | 4-bromothenyl | 253, 343 | 5.79(s), 7.49(d, 1.6), 7.81(d, 1.6), 7,95(s), 8.01(s). |
| Type 3B. 8-Thiaguanines | | | |
| B. 4296 | benzyl | 227, 361 | |
| B. 4286 | 4-fluorobenzyl | 235, 361 | 5.59(s), 7.29(t 8.9), 7.51(bs), 7.67(m) |
| B. 4315 | 4-chlorothenyl | 228, 360 | 5.75(s), 7.44(d, 1.6), 7.55(bs), 7.69(d, 1.6). |
| B. 4351 | 4-bromothenyl | 228, 361 | 5.78(s), 7.45(d, 1.6), 7.46(bs), 7.75(d. 1.6) |
| Type 3C. Pterins (O⁴-substituent) | | | |
| B. 4290 | 4-fluorobenzyl | 232, 264(sh), 362 | 5.56(s), 7.29(t, 8.85), 7.44(bs), 7.66(m), 8.45(d, 1.8), 8.82(d, 1.8). |
| B. 4316 | 4-chlorobenzyl | 232, 364 | 5.71(s), 7.41(d, 1.6), 7.47(bs), 7.67(d, 1.6), 8.46(d, 2.0), 8.83(d, 2.0) |
| B. 4288 | 4-bromothenyl | 231, 364 | 5.73(s), 7.44(d, 1.6), 7.50(bs), 7.77(d, 1.6) 8.46(d, 2) 8.83(d, 2). |
| Type 4A. 2,4-diamino-6-hydroxy-pyrimidines | | | |
| B. 4305 | 4-fluorobenzyl | | 5.10(s), 5.19(s), 5.96(s), 6.10(s), 7.19(t, 8.8), 7.44(dd, 8.8, 5.8). |
| B. 4304 | 4-chlorobenzyl | | 5.11(s), 5.22(s), 5.96(s), 6.10(s), 7.44(s). |
| B. 4303 | piperonyl | | 5.09(s), 5.12(s), 5.97(s), 6.03(s), 6.07(s), 6.91(d, 1.1), 7.00(s). |
| B. 4307 | thenyl | | 5.08(s), 5.40(s), 6.00(s), 6.10(s), 7.03(dd, 3.1, 3.5)7.20(dd, 8.1, 1.1), 7.54 (dd, 3.5, 1.1). |
| B. 4302 | 4-chlorothenyl | | 5.08(s), 5.35(s), 6.03(s), 6.3(s), 7.19(s), 7.55(d, 1.6). |
| Type 4B. 2,4-Diamino-6-hydroxy-5-nitrosopyrimidines | | | |
| B. 4301 | 4-fluorobenzyl | 336 | 5.59(s), 7.26(m), 7.65(m), 7.80(bs), 7.86(bs), 8.00(bs), 10.05(bs). |
| B. 4311 | 4-chlorothenyl | 335 | 5.73(s), 7.40(d, 1.6), 7.66(d, 1.6), 7.94(s), 7.98(d, 2.7), 8.10(d, 4.2) 10.03 (d, 4.2). |
| B. 4312 | 4-bromothenyl | 335 | 5.75(s), 7.42(d, 1.4), 7.75(d, 1.4), 7.93(s), 7.98(s), 8.12(d, 4.0), 10.04 (d, 4.0) |
| Type 4C. 2,4-diamino-6-hydroxy-5-nitropyrimidines | | | |
| B. 4308 | piperonyl | 288, 330 | 5.33(s), 6.05(s), 6.95(d, 8.0), 7.00(dd, 8.0, 1.4), 7.10(d, 1.4), 7.26(bs), 7.3 7.96(bs). |
| B. 4306 | thenyl | 234, 329 | 5.59(s), 7.03(dd, 5.1, 3.5), 7.28(d, 3.5), 7.32(bs), 7.56(d, 5.1), 7.94(bs). |

TABLE 2

| | INACTIVATOR TYPE | $I_{50}(\mu M)$ |
|---|---|---|
| 1A | B.4291 O⁶ (thenyl)-hypoxanthine | 1.9 |
| | B.4293 O⁶-(furfuryl)-hypoxanthine | 28 |
| | B.4292 O⁶-(4-bromothenyl)-hypoxanthine | 0.3 |
| | O⁶-(benzyl)-hypoxanthine[b] | 85 |
| 1B | B.4347 O⁶-(benzyl)-2-methylhypoxanthine | 75 |
| | B.4350 O⁶-(thenyl)-2-methylhypoxanthine | 14 |
| 1C | B.4353 O⁶ (4 bromothenyl)-2-fluoro,hypoxanthine | |
| | O⁶-(benzyl)-2-fluorohypoxanthine[a] | 48 |
| 1D | B.4334 O⁶-(benzyl)-9-(2-hydroxyethoxymethyl)guanine | 8 |
| | B.4335 O⁶-(4 bromothenyl)-9-(2-hydroxyethoxymethyl)guanine | 0.33 |
| 1E | B.4349 O⁶-(4-bromothenyl)-8-hydroxyguanine | 0.018 |
| | O⁶-(benzyl)-8-hydroxyguanine[a] | 0.03 |
| 2A | B.4270 O⁶-(4-fluorobenzyl)-8-azaguanine | 0.08 |
| | B.4314 O⁶-(4-chlorobenzyl)-8-azaguanine | 0.011 |
| | B.4289 | 0.045 |
| | O⁶-(4-bromothenyl)-8-azaguanine | 0.07 |
| | O⁶-(benzyl)-8-azaguanine[a] | |
| 2B | B.4310 O⁶-(benzyl)-8-aza-7-deazaguanine | 0.0093 |
| | B.4340 O⁶-(4-fluorobenzyl)-8-aza-7-deazaguanine | 0.018 |
| | B.4339 O⁶-(4-chlorobenzyl)-8-aza-7-deazaguanine | 0.02 |
| | B.4343 O⁶-(piperonyl)-8-aza-7-deazaguanine | 0.0065 |
| | B.4348 O⁶-(furfuryl)-8-aza-7-deazaguanine | 0.036 |
| | B.4338 O⁶-(thenyl)-8-aza-7-deazaguanine | 0.01 |
| | B.4337 O⁶-(4-bromothenyl)-8-aza-7-deazaguanine | 0.007 |
| 3A | B.4272 O⁶-(4-fluorobenzyl)-8-oxaguanine | 0.02 |
| | B.4285 O⁶-(4-chlorobenzyl) 8 oxaguanine | 0.225 |
| | B.4299 O⁶(4-chlorothenyl)-8-oxaguanine | 0.243 |
| | B.4287 O⁶-(-4-bromothenyl)-8-oxaguanine | 0.24 |
| | B.4232 O⁶-(benzyl)-8-oxaguanine | 0.25 |

TABLE 2-continued

| INACTIVATOR TYPE | $I_{50}(\mu M)$ |
|---|---|
| 3B B.4296 | 0.02 |
| $\underline{O}^6$-(benzyl)-8-thiaguanine | |
| B.4286 | 0.03 |
| $\underline{O}^6$-(4-fluorobenzyl)-8-thiaguanine | |
| B.4315 | 0.006 |
| $\underline{O}^6$-(4-chlorothenyl)-8-thiaguanine | |
| B.4351 | 0.0028 |
| $\underline{O}^6$-(4-bromothenyl)-8-thiaguanine | |
| 3C B.4290 | 0.088 |
| $\underline{O}^4$-(4-fluorobenzyl)-pterin | |
| B.4316 | 0.025 |
| $\underline{O}^4$-(4-chlorothenyl) pterin | |
| B.4288 | 0.025 |
| $\underline{O}^4$-(4-bromothenyl)-pterin | |
| 4A B.4305 | 4.0 |
| 2,4-diamino-6-(4-fluorobenzyloxy)pyrimidine | |
| B.4304 | 5.0 |
| 2,4-diamino-6-(4-chlorobenzyloxy)pyrimidine | |
| B.4303 | 0.8 |
| 2,4-diamino-6-(3,4-piperonyloxy)pyrimidine | |
| B.4307 | 0.4 |
| 2,4-diamino-6-(thenyloxy)pyrimidine | |
| B.4302 | 0.17 |
| 2,4-diamino-6-(4-chlorothenyloxy)pyrimidine | |
| 2,4-diamino-6-(benzyloxy)pyrimidine[a] | 15 |
| 4B B.4301 | 0.0175 |
| 2,4-diamino-6-(4-fluorobenzyloxy)-5-nitrosopyrimidine | |
| B.4311 | 0.009 |
| 2,4-diamino-(4-chlorothenyloxy)-5-nitrosopyrimidine | |
| B.4312 | 0.045 |
| 2,4-diamino-6-(4-bromothenyloxy)-5-nitrosopyrimidine | |
| 2,4-diamino 6-(benzyloxy)-5-nitrosopyrimidine[a] | 0.06 |
| 4C B.4306 | 2.3 |
| 2,4-diamino-6-(thenyloxy)-5-nitropyrimidine | |
| B.4308 | 0.5 |
| 2,4-diamino-6-piperonyloxy-5-nitropyrimidine | |
| 2,4-diamino-6-benzyloxy-5-nitropyrimidine[a] | 0.06 |

[a]Data taken from Chae et al, J. Med. Chem. 1995, 38, 359–365
[b]Data taken from Moschel et al., J. Med. Chem. 1992, 35, 4486–4491.

References

1. Kiburis J. and Lister, J. H. *J. Chem. Soc*, (C), 1971, 3942.

2. Robins R. K., Jones, J. W. and Lin, H. H., *J. Org. Chem.* 21, 1956, 695.

3. Robins R. K. and Robins, M. J. *J. Org. Chem.*, 34 1969, 2163.

4. Robins, M. J. and Hatfield, P. W., *Canad J. Chem.*, 60, 1982, 547.

5. Dolan, M. E., Chae, M.-Y., Pegg. A. E., Mullen, J. H., Friedmnan, H. S. and Moschel, R. C. *Cancer Res.*, 54, 1994, 5123.

6. Shealy, Y. F., Clayton, J. D., O'Dell, G. A. and Montgomery, J. A., *J. Org. Chem.*, 27, 1962, 4518.

7. Seela, F., Steker, H., Driller, H. and Bindig, U., *Liebigs Ann. Chem.*, 1987, 15.

8. Boyle, P. H. and Lockhart, R. J., *Tetrahedron*, 40, 1984, 879.

9. Kresze, C. and Wucherpfennig, W., *Newer Methods of Preparative Organic Chemistry* (W. Foerst, ed.), Academic Press, New York, 1968, vol. 5, p.115; Shealy, Y. F., Clayton, J. D. and Montgomery, J. A., *J. Org. Chem.*, 27, 1962, 2154.

10. Baudy, R. B., Greenblatt, L. P. et al., *J. Med. Chem,*. 36, 1993, 331.

11. O'Brien, D. E. Cheng, C. C. and Pfleiderer, W., *J. Med. Chem.*, 9 1966, 573; Rokos, H. and Pfleiderer, W., *Chem. Ber.*, 104, 1971, 739.

We claim:

1. A pyrimidine derivative selected from

A) 6-hetarylalkyloxy pyrimidine derivatives of formula II

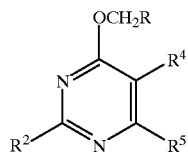

II wherein

R is a cyclic group having at least one 5- or 6-membered heterocyclic ring, optionally with a carbocyclic or heterocyclic ring fused thereto, the or each heterocyclic ring having at least one hetero atom selected from the group consisting of O, N and S, or a substituted derivative thereof having substitution of the heterocyclic ring(s) and/or carbocyclic ring(s) by one or more substituents selected from the group consisting of alkyl, alkenyl, alkynyl, halo, haloalkyl, nitro, cyano, hydroxyalkyl, alkylenedioxy, $SO_nR''''$ where $R''''$ is alkyl and n=0, 1 or 2, and a carboxyl or ester group of the formula —$COOR^e$ where $R^e$ is H or alkyl;

$R^2$ is a member selected from the group consisting of H, $C_1$–$C_5$ alkyl, halogen and $NH_2$;

$R^4$ and $R^5$ which are the same or different are selected from the group consisting of H, $NH_2$ and $NO_{n'}$, where n'=1 or 2; or $R^4$ and $R^5$ together form a ring structure $III^a$

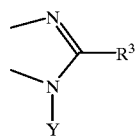

$III^a$ wherein

Y is H, $HOCH_2CH_2OCH_2$-, ribosyl, deoxyribosyl, arabinosyl, or

wherein X is O or S, R″ and R′″ are alkyl or substituted derivatives thereof having substitution by one or more substituents selected from the group consisting of hydroxy, halo, alkoxy, amino, alkylamino, amido and ureido, $R^3$ is H or OH; or $R^4$ and $R^5$ together with the pyrimidine ring form a 5- or 6- membered ring structure containing one or more hetero atoms other than that of formula $III^a$ above, and pharmaceutically acceptable salts thereof, provided that if $R^4$ and $R^5$ form a ring structure IX

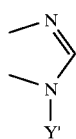

IX wherein

Y' is H, ribosyl, deoxyribosyl, or

wherein X is O or S, R" and R'" are alkyl, or substituted derivatives thereof, $R^2$ is not $NH_2$; and B) 6-arylalkyloxy pyrimidine derivatives selected from those of formulae $III^b$, $III^c$, $IV^b$, $V^b$, $VI^b$, $VI^b$ and $VII^b$ as defined below:

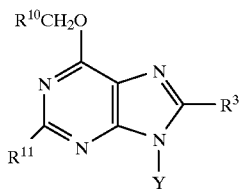

$III^b$ wherein $R^{10}$ is phenyl or a substituted derivative thereof having substitution by one or more substituents selected from the group consisting of alkyl, alkenyl, alkynyl, halo, haloalkyl, nitro, cyano, hydroxyalkyl, alkylenedioxy and $SO_nR""$ where $R""$ and n are as defined for formula II or a carboxyl or ester group of the formula —$COOR^c$ wherein $R^c$ is as defined for formula II;

$R^{11}$ is $C_1$–$C_5$ alkyl;

Y is as defined above;

$III^c$ wherein $R^{10}$ is as defined above;

$R^2$ is as defined for formula II;

$R^3$ is H or OH;

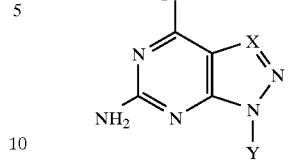

$IV^b$ wherein $R^{10}$ is as defined above;

Y is as defined for formula $III^a$;

X is CH or N;

provided that if X is N and Y is H, then $R^{10}$ is not phenyl;

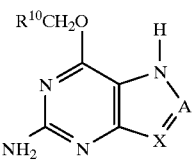

$V^b$ wherein $R^{10}$ is as defined above;

X is CH or N;

A is CH or N;

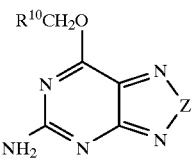

$VI^b$ wherein $R^{10}$ is as defined above;

Z is O or S or CH=CH;

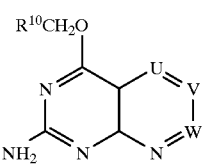

$VII^b$ wherein $R^{10}$ is as defined above;

U is CH or N;

V is CH or N;

W is CH or N;

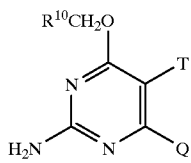

VIII<sup>b</sup> wherein

R<sup>10</sup> is as defined above;

T is H, NH$_2$ or NO$_n$ where n=1 or 2;

Q is H, NH$_2$ or NO$_n$ where n=1 or 2;

provided that:
if Q is NH$_2$ and T is NO or NO$_2$, or
if Q is H and T is NO$_2$, or
if Q and T are both NH$_2$, or
if Q is NH$_2$, and T is H, then R$^{10}$ is not phenyl.

2. A 6-hetarylalkyloxy pyrimidine derivative according to claim 1 which is of Formula III

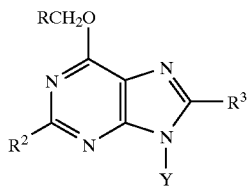

III wherein:

R is as defined in claim 1;

Y is H or HOCH$_2$CH$_2$OCH$_2$-;

R$^2$ is as defined in claim 1;

R$^3$ is as defined in claim 1;

provided that if Y and R$^3$ are both H, R$^2$ is not NH$_2$.

3. A 6-hetarylalkyloxy pyrimidine derivative according to claim 1 which is of Formula IV

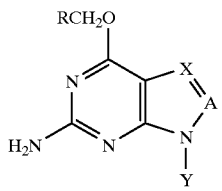

IV wherein:

R and Y are as defined in claim 1;

X is CH or N;

A is CH or N;

provided that if X is N and A is CH, then

Y is not Y' as defined in claim 1.

4. A compound according to claim 1 which is of Formula V

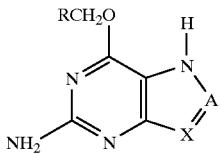

V wherein:

R is as defined in claim 1

X is CH or N

A is CH or N.

5. A compound according to claim 1 which is of Formula VI

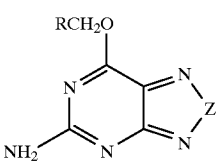

VI wherein:

R is as defined in claim 1;

Z is O or S or CH=CH.

6. A compound according to claim 1 which is of Formula VII

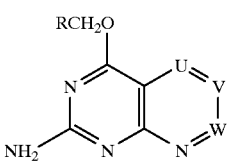

VII wherein:

R is as defined in claim 1;

U is CH or N;

V is CH or N;

W is CH or N.

7. A compound according to claim 1 which is of Formula VIII

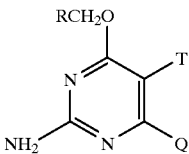

VIII wherein:

R is as defined in claim 1

T is H, NH$_2$ or NO$_n$ where n=1 or 2;

Q is H, NH$_2$ or NO$_n$ where n=1 or 2.

8. A compound according to claim 1 wherein R is:
(a) a 5- or 6- membered heterocyclic ring, or
(b) a 5- or 6- membered heterocyclic ring having a carbocyclic ring fused thereto to form a benzo derivative thereof, the 6-alkyloxypyrimidine moiety being attached to R at either the heterocyclic or the benzene ring.

9. A compound according to claim 1 wherein R is a 5 membered heterocyclic ring, having at least one S heteroatom therein.

10. A compound according to claim 1 wherein R as defined in claim 1 is selected from a thiophene ring, a furan ring, and substituted derivatives thereof.

11. A compound according to claim 1 wherein R includes a heterocyclic and/or carbocyclic ring substituted by halo, haloalkyl, cyano, $SO_nR''''$ where $R''''$ is alkyl and n=0, 1 or 2 or —$COOR^5$ wherein $R^c$ is alkyl.

12. A compound according to claim 1 wherein R is selected from a thiophene ring, a furan ring and substituted derivatives thereof selected from bromo- and cyano-substituted derivatives.

13. A compound according to claim 1 wherein R is selected from thiophene and furan rings with a chloro-, bromo- or cyano-substituent in a 1,3 or 1,4-relationship in the thiophene or furan ring with the methyleneoxy group attached to the pyrimidine residue.

14. A pharmaceutical composition comprising a compound according to claim 1 and a pharmaceutically acceptable excipient.

15. A pharmaceutical composition according to claim 14 further comprising an alkylating agent.

16. A composition according to claim 15 wherein the alkylating agent is selected from 1,3 bis (2-chloroethyl)-1-nitrosourea (BCNU) and to 8-carbamoyl-3-methylimidazo[5,1-d]-1,2,3,5-tetrazin-4 (3H)-one (temozolomide).

17. A method for depleting $\underline{O}^6$-alkylguanine-DNA alkyltransferase activity in a host in need thereof comprising:

administering to the host an effective $\underline{O}^6$-alkylguanine-DNA alkyltransferase activity depleting amount of a composition according to claim 14.

18. A method for treating alkylating-agent-sensitive tumor cells in a host comprising:

administering to the host in need thereof a composition according to claim 14 in an amount effective to deplete $\underline{O}^6$-alkylguanine-DNA alkyltransferase activity sufficiently to enhance the effectiveness of a chemotherapeutic alkylating agent;

and subsequently or simultaneously administering to the host a composition comprising an alkylating agent in an amount which is cytoxically effective in combination with the inactivator compound.

19. A pyrimidine derivative selected from the group consisting of $\underline{O}^6$-(4-bromothenyl)-9-(2-hydroxyethoxymethyl)guanine, $\underline{O}^6$-(4-bromothenyl)-8-hydroxyguanine, $\underline{O}^6$-(4-chlorothenyl)-8-azaguanine, $\underline{O}^6$-(piperonyl)-8-aza-7-deazaguanine, $\underline{O}^6$-(4-fluorobenzyl)-8-oxaguanine, $\underline{O}^6$-(4-bromothenyl)-8-thiaguanine, $\underline{O}^6$-(4-chlorothenyl)pterin and 2,4-diamino-(4-chlorothenyloxy)-5-nitrosopyrimidine.

* * * * *